(12) United States Patent
Ahern et al.

(10) Patent No.: US 11,020,549 B2
(45) Date of Patent: Jun. 1, 2021

(54) DRY POWDER INHALER WITH REPRODUCIBLE FLOW RESISTANCE

(71) Applicant: Alfred E. Tiefenbacher (GmbH & Co. KG), Hamburg (DE)

(72) Inventors: David Ahern, Cambridge (GB); Arron Danson, Eyeworth (GB); James Tibatts, Cambridge (GB); Ewen Christie, Cambridge (GB); Tim Evans, Cambridge (GB)

(73) Assignee: Alfred E. Tiefenbacher (GmbH & Co. KG), Hamburg (DE)

( * ) Notice: Subject to any disclaimer, the term of this patent is extended or adjusted under 35 U.S.C. 154(b) by 372 days.

(21) Appl. No.: 15/676,217

(22) Filed: Aug. 14, 2017

(65) Prior Publication Data

US 2018/0043111 A1 Feb. 15, 2018

Related U.S. Application Data

(60) Provisional application No. 62/448,515, filed on Jan. 20, 2017.

(30) Foreign Application Priority Data

Aug. 15, 2016 (EP) ..................................... 16184164

(51) Int. Cl.
*A61M 15/00* (2006.01)
*A61M 11/00* (2006.01)

(52) U.S. Cl.
CPC ...... *A61M 15/0086* (2013.01); *A61M 11/003* (2014.02); *A61M 15/002* (2014.02);
(Continued)

(58) Field of Classification Search
CPC .............. A61M 15/00; A61M 15/0021; A61M 15/0023; A61M 15/0025; A61M 15/0026;
(Continued)

(56) References Cited

U.S. PATENT DOCUMENTS

D355,029 S    1/1995  Kinneir et al.
5,947,118 A * 9/1999  Hochrainer ....... A61M 15/0028
                                                128/203.12
(Continued)

FOREIGN PATENT DOCUMENTS

EP        3138601 A1 *  3/2017  .......... A61M 15/003
WO     2015166239 A1    11/2015

OTHER PUBLICATIONS

European Search Report for pending European Application EP 16 18 4164 dated Jan. 20, 2017.
(Continued)

*Primary Examiner* — Joseph D. Boecker
*Assistant Examiner* — Thomas W Greig
(74) *Attorney, Agent, or Firm* — David B. Gornish; Eckert Seamans Cherin & Mellott, LLC (57) ABSTRACT

A dry powder inhalation device is disclosed. In one optional aspect, the device includes a housing, a base plate, a receptacle for a medicament and a mouthpiece. The base plate is engageable with the housing to form a main space with a main air inlet. The mouthpiece includes an inner conduit connected to its outlet and is engageable with the base plate to fluidly connect the inner conduit to the receptacle. The receptacle is fluidly connected to the main space, so that upon inhalation by a user, air can be drawn through the main air inlet into the main space and onward through the receptacle into the inner conduit. The mouthpiece and the base plate form an auxiliary space with an auxiliary air inlet, wherein the auxiliary space is fluidly connected to the main space.

27 Claims, 7 Drawing Sheets (52) U.S. Cl.
CPC ...... *A61M 15/003* (2014.02); *A61M 15/0023* (2014.02); *A61M 15/0026* (2014.02); *A61M 15/0035* (2014.02); *A61M 15/0041* (2014.02); *A61M 2202/064* (2013.01)

(58) Field of Classification Search
CPC ............ A61M 15/0028; A61M 15/003; A61M 15/0035; A61M 15/0033; A61M 15/0036; A61M 15/004; A61M 15/0041; A61M 15/0043; A61M 15/0086; A61M 5/0038
See application file for complete search history.

(56) References Cited

U.S. PATENT DOCUMENTS

| | | | | |
|---|---|---|---|---|
| 6,435,177 B1* | 8/2002 | Schmidt | ............ | A61M 15/0086 128/200.23 |
| 7,284,553 B2* | 10/2007 | Hochrainer | ....... | A61M 15/0028 128/203.21 |
| 8,022,082 B2 | 9/2011 | Zierenberg | | |
| 8,522,775 B2* | 9/2013 | Malhotra | .......... | A61M 15/0026 128/203.15 |
| 9,616,765 B2* | 4/2017 | Yamatani | ................ | B60K 1/04 |
| 2003/0015195 A1* | 1/2003 | Haaije de Boer | .......................... | A61M 15/0086 128/203.15 |
| 2003/0235538 A1* | 12/2003 | Zierenberg | ........ | A61M 15/0086 424/46 |
| 2004/0136919 A1 | 7/2004 | Hartig et al. | | |
| 2006/0237016 A1* | 10/2006 | Wachtel | ............ | A61M 15/0028 128/205.21 |
| 2009/0165791 A1* | 7/2009 | Wendland | .......... | A61M 15/0028 128/203.21 |
| 2009/0314291 A1* | 12/2009 | Anderson | ......... | A61M 15/0075 128/203.15 |
| 2010/0275917 A1* | 11/2010 | Kuhn | ................ | A61M 15/0028 128/203.15 |
| 2011/0232637 A1* | 9/2011 | Kaemper | ......... | A61M 15/0028 128/203.12 |
| 2011/0259328 A1 | 10/2011 | Villax et al. | | |
| 2014/0318538 A1* | 10/2014 | Bilgic | ................ | A61M 15/0028 128/203.15 |
| 2016/0022931 A1* | 1/2016 | Althorpe | .......... | A61M 15/0028 128/203.12 |

OTHER PUBLICATIONS

Boehringer Ingelheim Boehringer Ingelheim, "How to Use Your HandiHaler—SPIRIVA HandiHaler", (Apr. 30, 2014), URL:https://www.spiriva.com/pdf/copd/SPIRIVA_HandiHaler_Instructions.pdf, (retrieved Jan. 19, 2017).

* cited by examiner

DRY POWDER INHALER WITH REPRODUCIBLE FLOW RESISTANCE

BACKGROUND OF THE INVENTION

In a dry powder inhaler, an air stream generated by inhalation of the user entrains a powdered medicament for delivery to the lungs of the user. The medicament usually needs to be provided in very small particles, a few microns or less in size, that can bypass the protective mechanisms of the respiratory tract and actually reach the lungs. For handling of the medicament up to the point of the actual inhalation, on the other hand, the medicament needs to have a far larger particle size. To this end, the active ingredient of the medicament is usually attached to an inactive excipient. During inhalation, the active ingredient is detached (deagglomerated) from the excipient by the force of the air flow, so that the active ingredient enters the user's lungs, while the excipient stays behind.

U.S. Pat. No. 8,022,082B2 discloses a dry powder inhaler with a housing, a base plate, a receptacle for a medicament and a mouthpiece. The base plate is engageable with the housing to form a space with an air inlet. When the user inhales through the mouthpiece, air is drawn through the air inlet. Part of this air is drawn through the receptacle and entrains the medicament. A smaller portion of the air is added to the medicament-laden air on a bypass air path without having passed through the receptacle first.

The actual dose of the medicament delivered to the user's lungs depends on the total amount of medicament powder entrained by the air stream and on the efficiency of the deagglomeration. Both parameters vary greatly with the flow resistance of the inhaler. It is therefore important that the inhaler reproducibly exhibits the same flow resistance upon every use, and that the flow resistance does not vary too much among a batch of mass-produced inhalers.

In one aspect, therefore, it is a preferred objective of the present invention to provide a dry powder inhaler with a more reproducible flow resistance. The objective of this, in turn, is to ensure a consistent deagglomeration of the medicament powder as the prime objective.

This objective is achieved by an inhaler according to one of the independent claims. The dependent claims provide further advantageous embodiments.

BRIEF SUMMARY OF THE INVENTION

The inventors have developed a dry powder inhalation device. In a first aspect, this device comprises a housing, a base plate, a receptacle for a medicament and a mouthpiece. The base plate is engageable with the housing to form a main space with a main air inlet. The mouthpiece comprises an inner conduit connected to its outlet. To fluidly connect the inner conduit to the receptacle, the mouthpiece is engageable with the base plate. The receptacle is in turn fluidly connected to the main space, so that upon inhalation by the user, air can be drawn through the main air inlet into the main space and onward through the receptacle into the inner conduit.

According to the first aspect of the invention, the mouthpiece and the base plate form an auxiliary space with an auxiliary air inlet. The auxiliary space is fluidly connected to the main space.

The inventors have found that if an inhaler has only a main air inlet, this main air inlet can be inadvertently obstructed at least partially when the device is being hand-held. Such obstruction increases the flow resistance and therefore alters the actual dose of medicament delivered to the user's lungs. The probability of both air inlets being obstructed at the same time is low, so there will be at least one unobstructed airway into the inhaler in almost all cases, leading to a reproducible flow resistance and a constant delivered dose upon every use.

This effect is most pronounced in an advantageous embodiment of the invention where the flow resistance of each of the main air inlet and the auxiliary air inlet is lower than the flow resistance of the path between the main space and the mouthpiece outlet, and lower than the flow resistance of the path between the auxiliary space and the mouthpiece outlet. In this manner, even if one of the main air inlet and the auxiliary inlet is totally obstructed, the remaining inlet will not be the limiting factor for the total flow resistance of the inhaler.

To guard against inadvertent obstruction of the air inlets, in a further advantageous embodiment of the invention, the main air inlet, and/or the auxiliary air inlet, comprises a recess in the base plate.

Preferably, the recess that forms part of the main air inlet is formed in an area where the base plate is hinged to the housing. In this manner, the hinge can be exploited as an additional mechanical guard against a finger obstructing the main air inlet.

Preferably, the recess that forms part of the auxiliary inlet is formed in an area where the base plate is set in a further recess in the housing. In this manner, the recess in the base plate can be made larger, so that it becomes more unlikely that it will be obstructed by a finger of a hand holding the device.

To further reduce the probability of a finger obstructing the auxiliary air inlet, the housing may preferably have an oval shape comprising two flat side faces and two curved side faces, with the further recess being placed in at least one of the flat side faces.

In a second aspect of the invention, the dry powder inhalation device comprises a housing, a base plate with a receptacle for a medicament and a mouthpiece. The base plate is engageable with the housing to form a main space. The mouthpiece comprises an inner conduit connected to its outlet. The mouthpiece is engageable with the base plate to fluidly connect the inner conduit to the receptacle. A first airway is provided between the main space and atmosphere, so that upon inhalation by the user, air can be drawn through said airway into the main space and onward through the receptacle into the inner conduit.

According to the second aspect of the invention, the mouthpiece and the base plate form an auxiliary space. The auxiliary space is fluidly connected to atmosphere by a second airway and to the inner conduit by means of a bypass air path.

The first airway may, for example, comprise a main air inlet, and the second airway may, for example, comprise an auxiliary air inlet, as per the first aspect of the invention. However, both the main space and the auxiliary space may, for example, also be supplied with air by one and the same air inlet. For example, if the auxiliary space is fluidly connected to the main space, as per the first aspect of the invention, both the main space and the auxiliary space may be supplied with air through one single air inlet, e.g., the main air inlet or the auxiliary air inlet.

The second aspect of the invention tackles a different source of error for the flow resistance than the first aspect. Because of inevitable manufacturing tolerances in the mass-production of inhalers, the base plate, the housing, the mouthpiece and the inner conduit of the mouthpiece will not form perfect seals with each other. Rather, there will be diverse leakage paths, which will vary among different inhalers in a mass-produced batch. Such variation may especially occur when new or reworked tools are used.

If a bypass air path is present and its flow resistance is kept sufficiently constant among the different inhalers in the batch, the effect of the leakage paths on the total flow resistance of the inhaler will be reduced by this variation. The inventors have found that it is far easier to manufacture a deliberate leakage path with a sufficiently constant flow resistance than to manufacture all components of the inhaler precisely enough to keep the flow resistances of all leakage paths constant.

The inventors have found that, surprisingly, providing the bypass air path specifically between the auxiliary space and the inner conduit permits a most reproducible and at the same time cost-effective mass-manufacturing of the bypass air path. The flow resistance may be readily tuned to a greater extent than in the prior art inhaler.

The effect is most pronounced in an especially advantageous embodiment of the invention where the flow resistance of the bypass air path is lower than the flow resistance of the combination of all leakage paths in the device. Variations in the leakage paths will then no longer have a noticeable effect on the total flow resistance of the inhaler.

It should be noted that, while each aspect of the invention improves the reproducibility and stability of the flow resistance on its own, both aspects may, in an especially advantageous embodiment of the invention, synergistically work together in one single inhaler for best results.

Preferably, the inner conduit is connectable to the receptacle via a screen held in a screen holder. This screen may, for example, comprise a mesh with apertures of the order of 1 mm.

The main function of the screen is to set a range within which a capsule with medicament powder will reciprocate along the axis of the receptacle during inhalation, thus keeping the capsule from being sucked up into the mouthpiece and jamming its airway. The screen will provide one endpoint (ceiling) for this reciprocating motion, which in turn impacts the actual dynamic flow resistance of the inhaler, when the base plate is engaged with the housing. Furthermore, the reciprocating motion does influence the powder evacuation, and therefore also the delivered dose to the lungs of the user.

The secondary function of the screen is to prevent larger foreign objects, such as remnants of a packaging of the medicament, chads and other detritus from being passed to the outlet of the mouthpiece. As a side effect, the screen also contributes to the flow resistance of the inhaler. Specifically, the screen holder may form part of the inner conduit of the mouthpiece.

In an especially advantageous embodiment of the invention, the bypass air path comprises at least one opening and/or recess in the screen holder. In this manner, it becomes particularly easy and cost-efficient to manufacture different inhalers with bypass air paths having different defined flow resistances. To change the flow resistance, only the screen holder needs to be changed.

It should be noted that changing the height or the shape of the screen will have a quantitatively far larger effect (by about a factor of 10) on the overall flow resistance of the inhaler than changing a bypass opening and/or recess in the screen holder. In addition, as discussed above, the bypass air path needs to support a higher flow than the unintentional leak paths to ensure a reproducible deagglomeration, which constrains how much the flow through the bypass air path can be reduced. If a significantly lower total flow through the inhaler is desired, it is therefore advisable to change the position and/or the shape of the screen, and/or the diameter of the air inlet into the receptacle.

It should also be noted that the flow resistance is not per se a sufficient criterion for an optimum performance of the inhaler. Though certain patients may require the flow resistance of the inhaler to be in a specific range, it is the deagglomeration capability for the medicament that primarily defines the optimum performance. This is connected to the flow resistance and to the total flow, but not in a fixed relationship. The shape of air paths and the contact surfaces, as well as swirls or other disturbances in the flow, may have greater effects on the deagglomeration than the flow resistance, and two devices with identical flow resistances may have radically different performances in terms of deagglomeration. The primarily advantageous effect of the invention is not the provision of ways to set an arbitrary flow resistance, but rather a greatly improved reproducibility in the flow resistance: the deagglomeration will not be unintentionally altered by an unintentional variation in the flow resistance.

In a further especially advantageous embodiment of the invention, the bypass air path further comprises at least one opening and/or recess in the base plate that cooperates with the opening and/or recess in the screen holder. "Cooperating" means that the openings and/or recesses in the two parts work together to enclose the cross section of a part of the bypass air path, and/or that each of the openings and/or recesses encloses a section of the bypass air path, with the sections being concatenated.

Splitting up the bypass air path in this way allows for the manufacture of both parts of the air path with relatively simple tools. If different flow resistances are set by means of different screen holders, the opening and/or recess in the screen holder will remain the determining factor for the flow resistance of the bypass opening, so the cooperating opening and/or recess in the base plate may remain unchanged.

Preferably, the screen holder is click-mountable to the mouthpiece. An existing inhaler may then be switched to a different flow resistance simply by swapping out the screen holder. In addition, the screen is easier to clean should this ever become necessary.

Preferably, the screen holder has a circular circumference, and the bypass air path comprises at least four openings and/or recesses in a symmetric arrangement of angular positions along this circumference. This will produce a laminar flow of the bypass air. Specifically, a more uniform distribution of airflow over the convergent walls of the screen holder, and/or of the inner conduit of the mouthpiece, may be obtained compared with the prior art inhaler.

The openings and/or recesses may, for example, be recesses in the screen holder, especially in the perimeter of the screen holder, that cooperate with the base plate to form channels which contribute to the bypass air path. Preferably, at least one recess in the perimeter of the screen holder cooperates with the base plate to enclose a channel with a cross sectional area above 0.2 $mm^2$ and below 0.8 $mm^2$. Preferably, at least three such recesses are present. Most advantageously, four recesses are present.

The openings and/or recesses may also be, for example, holes in the screen holder. The difference between a hole and a recess is that a hole's circumference is wholly surrounded by the material of the screen holder. Preferably, at least one hole has a diameter above 0.5 mm and below 1 mm. Preferably, at least three such holes are present. Most advantageously, four holes are present.

For example, when the inhaler is in an upright position and ready to use, so that the receptacle is below the base plate and the screen holder is on top of the base plate, bypass air may be drawn in through the openings and/or recesses in the screen holder on to the openings and/or recesses in the base plate. The openings and/or recesses in the base plate will then reverse the flow of the bypass air. At the same time, the flow will also be equalized around an annulus formed between a central opening in the base plate that is to pass the medicament-laden air from the receptacle on the one hand, and the screen holder on the other hand. The bypass air stream will then be merged with the main medicament-laden air stream. The bypass air stream will slightly reduce the total flow resistance of the inhaler.

For different applications, it may be advantageous to provide an asymmetric arrangement of the openings and/or recesses, so as to induce swirls in the air flow that aid the deagglomeration of the active ingredient from the excipient.

In an especially advantageous embodiment of the invention, the base plate comprises at least one air exchange opening for connecting the auxiliary space to the main space. In this manner, no matter whether air enters the inhaler through the main space or through the auxiliary space, it will be available in the main space to entrain the medicament from the receptacle. If a bypass air path is present, the air will likewise always be available in the auxiliary space to be drawn into this bypass air path.

The medicament is preferably introduced into the receptacle in the form of capsules. Capsules are a convenient way of providing the medicament in pre-metered doses that can be easily handled while being protected from moisture and contamination right up to the moment when the medicament is inhaled. To release the medicament, in a further especially advantageous embodiment of the invention, the inhaler further comprises at least one piercing element that is movable into the receptacle by pushing a button against the force of a spring. When the button is pushed, the wall of the capsule is punctured. When the button is released, the spring retracts the piercing element, leaving a well-defined hole in the wall of the capsule through which the medicament can be extracted.

Most preferably, two piercing elements that are coupled to the same button and spring are provided to pierce the capsule in different positions along its longitudinal axis. In this manner, each actuation produces two holes in the wall of the capsule. One of these holes may then serve as an air inlet into the capsule, while the other hole may serve as an outlet for the medicament-laden air. If a screen is present, the screen ensures that no debris from the capsule wall is allowed to reach the outlet of the mouthpiece.

The piercing element may be specifically designed to leave a well-defined, retained "chad" on the capsule wall, so as not to detach any part of the capsule wall upon puncturing that wall. In this manner, no debris is produced that may be carried on with the air stream and cause a partial blockage further downstream.

Most preferably, at least one end stop is provided for the piercing element to keep it from completely traversing the receptacle. In this manner, it is ensured that only one wall of the capsule will be punctured, so every piercing element will only produce one hole. If the piercing element were able to completely penetrate the capsule, it would depend on the force applied to the button whether it produces one or two holes. The total dose delivered to the lungs of the user would then effectively depend on the force applied to the button.

In a further especially advantageous embodiment of the invention, a first piercing element with a first chamfered tip and a second piercing element with a second chamfered tip are provided. The chamfers of the two tips have opposite orientations in the direction of the longitudinal axis of the receptacle, i.e., the facet of the first chamfer is oriented towards one end of the longitudinal axis, while the facet of the other chamfer is oriented towards the other end of the longitudinal axis. In this manner, the forces that both piercing elements apply to the capsule in the direction of this longitudinal axis are collinear, equal and opposite, so they cancel each other out. With the facets facing outwards, these forces keep the side wall of the capsule in tension. Inward-facing facets would lead to a higher chance of buckling in the central section side-wall, or to crushing at the points of pierce contact due to the angle of the capsule wall at that point.

Preferably, the housing has a recess to accommodate the button. The receptacle, the piercing element and button may, for example, be mounted on one side of the base plate, while the mouthpiece may engage with the base plate on the other side of the base plate.

In a further especially advantageous embodiment of the invention, the housing, the base plate and the mouthpiece are hinged about a common axis of rotation. Even if the parts are engaged with each other and disengaged from each other with only one hand of the user, no part may then get lost.

Preferably, the device further comprises a lid for covering the mouthpiece when the inhaler is not in use. The lid may be hinged about the same axis of rotation.

BRIEF DESCRIPTION OF SEVERAL VIEWS OF THE DRAWINGS

In the following, the subject-matter of the invention is illustrated using Figures without any limitation of the claimed scope being intended. The Figures show:

FIG. 1: Exploded view of an optional embodiment of an inhaler.

FIG. 2: Sectional trimetric view of the inhaler of FIG. 1 in its assembled state.

FIG. 3*a*: Partial top view of the inhaler of FIG. 1 in its assembled state, illustrating aspects of the main air inlet of the inhaler.

FIG. 3*b*: Partial side view of the inhaler of FIG. 1 in its assembled state, illustrating aspects of the auxiliary air inlet of the inhaler.

FIG. 4: Sectional view detailing main air flow and bypass air flows.

FIG. 5*a*: Top view of a first optional embodiment of a screen holder.

FIG. 5*b*: Top view of a second optional embodiment of a screen holder.

FIG. 5*c*: Partial top view of the inhaler of FIG. 1 in a generally assembled state (with certain parts removed), illustrating the base plate.

FIG. 6*a*: Simplified sectional view of the inhaler of FIG. 1 in its assembled state, illustrating a first shuttling position.

FIG. 6*b*: Simplified sectional view of the inhaler of FIG. 1 in its assembled state, illustrating a second shuttling position.

The following reference signs are used in the Figures:

| Reference Sign | Description |
| --- | --- |
| 1 | Dry powder inhalation device (inhaler) |
| 1a | common axis of rotation |

-continued

| Reference Sign | Description |
| --- | --- |
| 2 | housing |
| 2a | recess in housing 2 for button 11 |
| 2b | windows in housing 2 |
| 2c | further recess in housing 2 for auxiliary air inlet 7a |
| 3 | base plate |
| 3a | air exchange opening in plate 3 between spaces 6 and 7 |
| 3b | recesses in base plate 3 for prongs 9c of screen holder 9 |
| 3c | central opening in base plate 3 |
| 4 | receptacle |
| 4a | longitudinal axis of receptacle 4 |
| 4b | bottom of capsule 4d |
| 4c | top of capsule 4d |
| 4d | capsule for insertion into receptacle 4 |
| 5 | mouthpiece |
| 5a | inner conduit of mouthpiece 5 |
| 5b | outlet of mouthpiece 5 |
| 6 | main space |
| 6a | main air inlet into main space 6 |
| 6b | recess in base plate 3 to provide main air inlet 6a |
| 7 | auxiliary space |
| 7a | auxiliary air inlet into auxiliary space 7 |
| 7b | recess in base plate 3 to provide auxiliary air inlet 7a |
| 8 | bypass air path from space 7 to inner conduit 5a |
| 8a | bypass opening and/or recess in screen holder 9 |
| 8b | bypass opening and/or recess in base plate 3 |
| 8c | annular bypass groove in base plate 3 |
| 9 | screen holder for screen 9a |
| 9a | screen in screen holder 9 |
| 9b | circumference of screen holder 9 |
| 9c | prongs of screen holder 9 for engagement with recesses 3b |
| 9d | grooves of screen holder 9 for rotational alignment |
| 10, 10a, 10b | piercing elements |
| 11 | button for actuation of piercing elements 10, 10a, 10b |
| 12 | spring |
| 13a, 13b | chamfered tips of piercing elements 10a, 10b |
| 14 | lid |
| 15 | axle |
| 16 | main air stream |
| 21, 22 | longer flat side faces of housing 2 |
| 23, 24 | shorter curved side faces of housing 2 |
| A | arrow |
| X | lower position of bottom 4b of capsule 4d |
| Y | upper position of top 4c of capsule 4d |

DETAILED DESCRIPTION OF PREFERRED
EMBODIMENTS OF THE INVENTION

Figure 1:
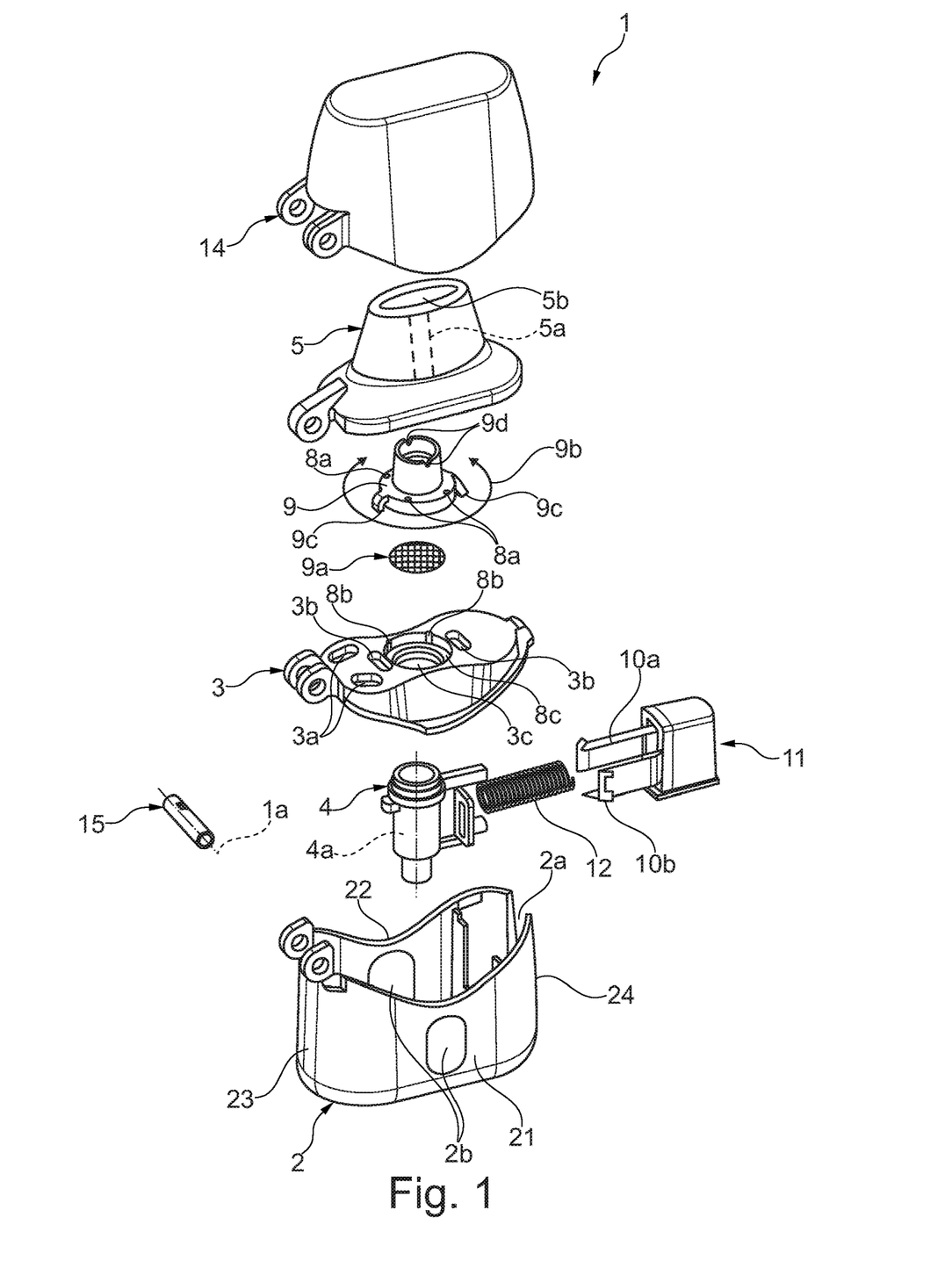

FIG. 1 shows an exploded view of an optional embodiment of a inhaler. The housing 2 has two windows 2b that provide a view of the receptacle 4 in the assembled state of the inhaler 1. The base plate 3 is hinged to the inhaler by means of an axle 15 that will form an axis of rotation 1a. Below the base plate 3, the receptacle 4 having a longitudinal axis 4a is mounted. Two piercing elements 10a and 10b may be pushed into the receptacle 4 by pressing the button 11 against the force of the spring 12. The housing 2 has a recess 2a for accommodating the button 11 in the assembled state of the inhaler 1. The housing 2 optionally has an oval shape with two longer flat side faces 21 and 22 and two shorter curved side faces 23 and 24.

The base plate (deck) 3 has air exchange openings 3a that connect the main space 6 and the auxiliary space 7, which are not shown in the exploded view of FIG. 1 for clarity. The base plate 3 has a central opening 3c through which air can pass from the receptacle 4 on to the mouthpiece 5. The central opening 3c is bordered by an annular groove 8c. On the perimeter of the annular groove 8c, the base plate 3 has four recesses 8b that lead into the annular groove 8c. In the perspective of FIG. 1, only two of the four recesses 8b are visible. The base plate 3 further comprises recesses 3b for engagement with corresponding prongs 9c of the screen holder 9.

The recesses 8a in the screen holder 9, the recesses 8b in the base plate 3 and the annular groove 8c in the base plate 3 together provide a bypass air path into the interior of the screen holder 9, and therefore into the inner conduit 5a of the mouthpiece 5.

The screen holder 9 primarily serves to mount a screen 9a into the airway from the receptacle 4 via the central opening 3c of the base plate 3 on to the mouthpiece 5. In addition, the screen holder 9 comprises four recesses 8a on its perimeter. The four recesses 8a, only three of which are visible in the perspective of FIG. 1, are in a symmetric arrangement of angular positions along a circular circumference 9b of the screen holder 9. The screen holder 9 further comprises grooves 9d on its top for rotational alignment.

After having passed the screen 9a, medicament-laden air is passed into the inner conduit 5a of the mouthpiece that is not visible in the perspective of FIG. 1. Since the screen holder 9 is click-mounted to this inner conduit 5a, it may be regarded as a part of the inner conduit 5a. At the outlet 5b, the air exits the mouthpiece 5 and enters the mouth of the user.

The mouthpiece 5 is mounted on the same axle 15, and is therefore rotatable about the same axis 1a, as the base plate 3 and the housing 2. When the inhaler 1 is not in use, the mouthpiece 5 is protected by a cover 15 that is mounted on the same axle 15 and rotatable about the same axis 1a.

Figure 2:
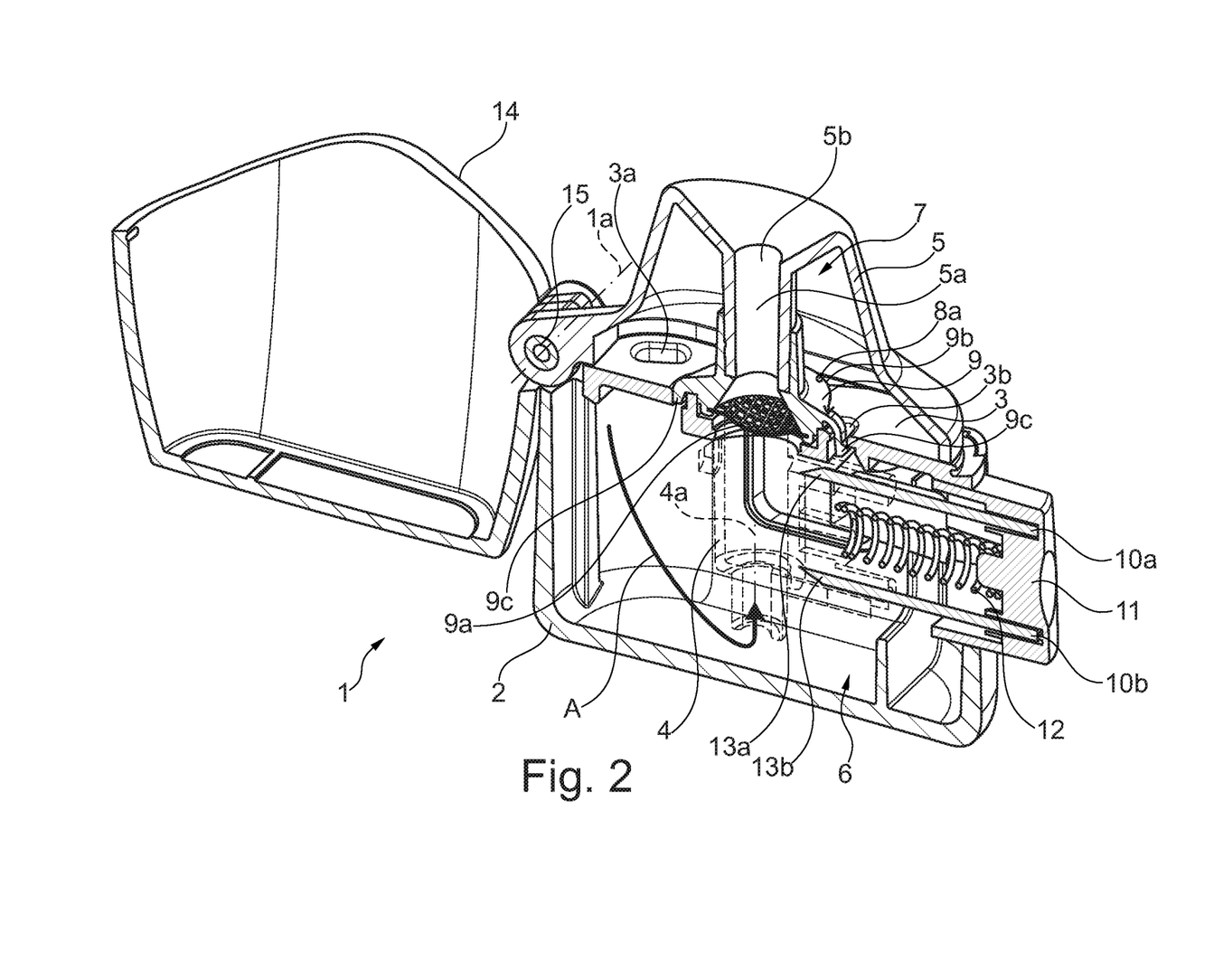

FIG. 2 shows a sectional trimetric view of the inhaler 1 in its assembled state. In this perspective, the main space 6 enclosed by the housing 2 and the base plate 3, as well as the auxiliary space 7 enclosed by the mouthpiece 5 and the base plate 3, become apparent. The main space 6 and the auxiliary space 7 are interconnected by the kidney-shaped air exchange openings 3a in the base plate 3, only one of which is visible in the perspective of FIG. 2. The arrow A in FIG. 2 illustrates how air passes from the main space 6 into the bottom of the receptacle 4. Because of the air exchange opening 3a, air can be scavenged from the auxiliary space 7 for this purpose as well.

The main air stream traverses the reservoir 4 from bottom to top along its longitudinal axis 4a, passes the screen 9a in the screen holder 9 and traverses the screen holder 9 from bottom to top on to the inner conduit 5a of the mouthpiece 5. Because the screen holder 9 is click-mounted and fluidly connected to the inner conduit 5a, it may be regarded as a part of this inner conduit 5a.

In the embodiment shown in FIG. 2, the screen holder 9 has four holes 8a in a symmetric arrangement around its circumference 9b. Only one hole 8a is visible in the perspective of FIG. 2.

FIG. 2 also details the piercing elements 10a and 10b. The tips 13a and 13b of the piercing elements 10a and 10b are each chamfered, with the chamfers having opposite orientations towards the longitudinal axis 4a of the receptacle 4. The facet of the first tip 13a faces upwards, while the facet of the second tip 13b faces downwards. When both tips 13a and 13b penetrate a capsule in the receptacle 4 simultaneously, the vertical forces exerted by both tips 13a and 13b onto the capsule are neutralized, and the capsule stays in place.

Figure 3A:
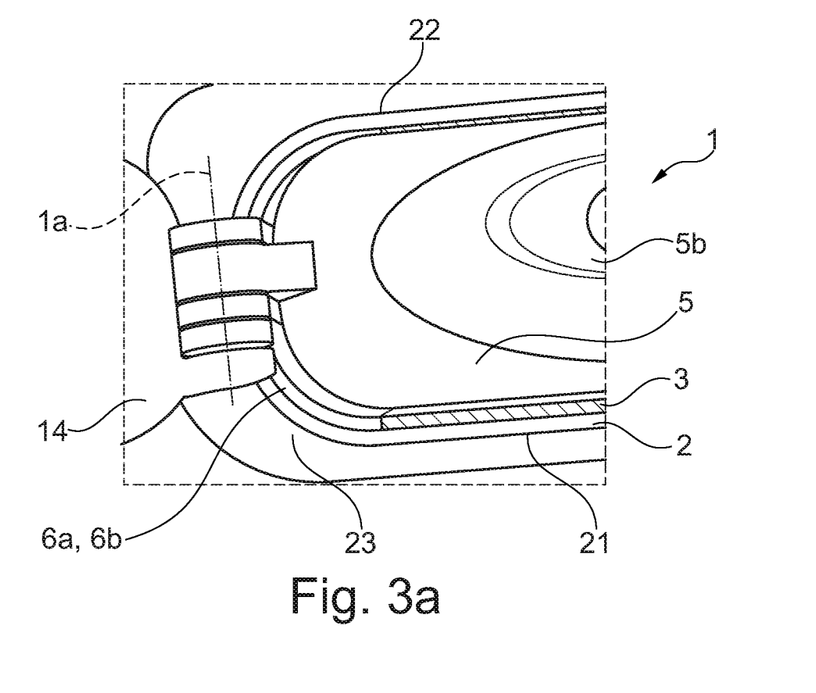
Figure 3B:
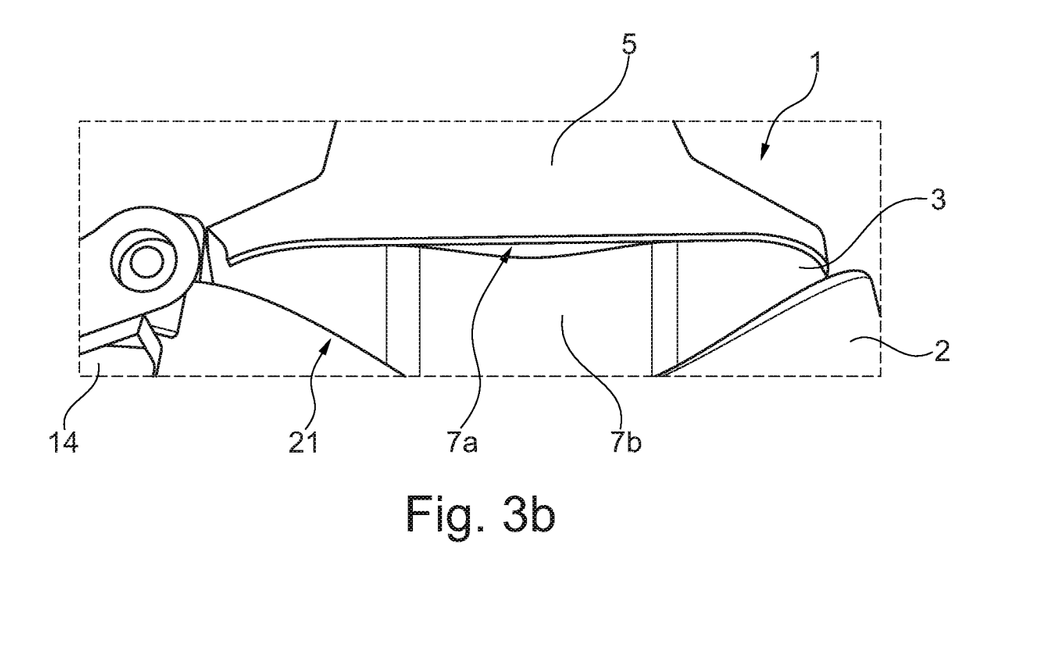

FIGS. 3a and 3b detail the positioning of the main air inlet 6a and the auxiliary air inlet 7a of the inhaler 1.

FIG. 3a is a top view of the inhaler 1; the outlet 5b of the mouthpiece 5 points out of the drawing plane. In the area where the housing 2 is hinged to the lid 14, a recess 6b is provided in the base plate 3. This recess 6b serves as the main air inlet 6a into the main space 6 enclosed by the base plate 3 and the housing 2. The hinge and the lid 14, which are present in the area of the main air inlet 6a, double to keep a finger of a hand holding the inhaler 1 from obstructing the main air inlet 6a.

FIG. 3b is a side view of the inhaler 1. The drawing plane is parallel to the longer flat side face 21 of the housing 2. The base plate 3, which is engaged with the mouthpiece 5, has a recess 7b. By means of this recess 7b, a gap is formed between the base plate 3 and the mouthpiece 5. This gap serves as the auxiliary air inlet 7a into the auxiliary space 7 that is enclosed between the mouthpiece 5 and the base plate 3. The auxiliary space 7 is not visible in the perspective of FIG. 3b; it is shown in the sectional trimetric view of FIG. 2.

Figure 4:
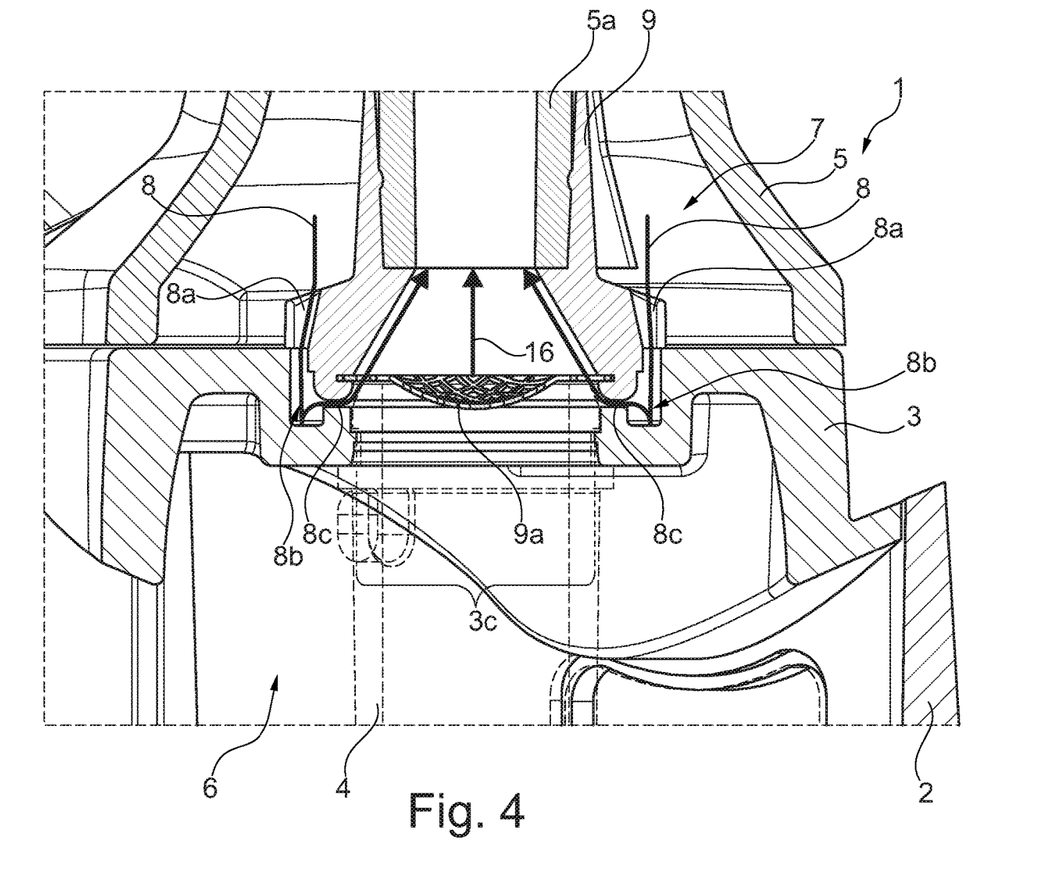

FIG. 4 is a partial sectional view of the inhaler 1 that details the providing of bypass air paths 8 in addition to the main air flow 16. From the auxiliary space 7, air passes through the holes 8a in the screen holder 9 that cooperate with recesses 8b in the base plate 3. Because the screen holder 9 abuts the base plate 3 in the area of the holes 8a, in the area of the annular groove 8c in the base plate 3 that surrounds the central opening 3c in the base plate 3, there is a gap between the lower part of the screen holder 9 and the base plate 3. Through this gap, the air can pass on from the recess 8b to the interior of the screen holder 9. In this manner, bypass air flows along bypass path 8, and then mixes with the main air flow 16 inside the inner conduit 5a of the mouthpiece 5.

Figure 5A:
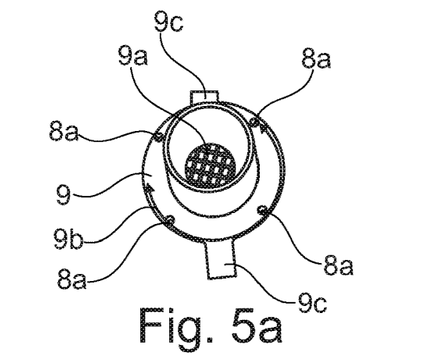
Figure 5B:
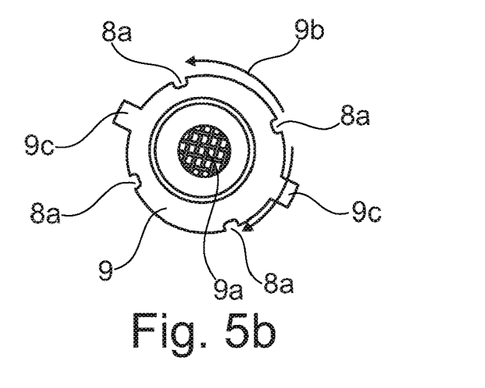
Figure 5C:
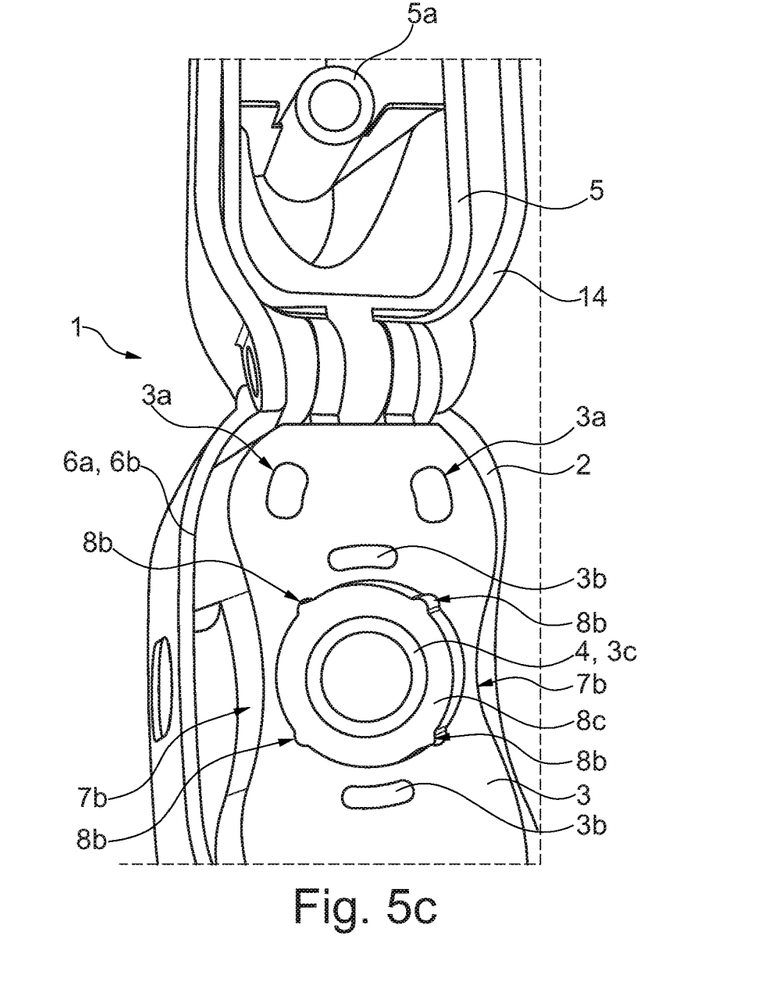

FIG. 5 further details the cooperation between openings and/or recesses 8a in the screen holder 9 with recesses 8b and an annular groove 8c in the base plate 3.

FIG. 5a shows a top view of a first embodiment of a screen holder 9. In a symmetric arrangement along the circular circumference 9b of the screen holder 9, four holes 8a are provided. FIG. 5b shows a top view of a second embodiment of a screen holder 9. In an analogous symmetric arrangement along the circular circumference 9b, four recesses 8a are provided in the perimeter of the screen holder 9.

FIG. 5c shows a top view of the inhaler 1 in a state where the lid 14 and the mouthpiece 5 have been disengaged from the housing 2 and base plate 3. The lid 14 and the mouthpiece 5 have been flipped over, and the screen housing 9 has been removed.

When the prongs 9c of the screen holder 9 are inserted into the corresponding recesses 3b in the base plate 3, the holes and/or recesses 8a of the screen holder 9 will be laterally aligned with the recesses 8b in the base plate 3. In this manner, bypass air will be passed on from the auxiliary space 7 through holes and/or recesses 8a in the screen holder 9, recesses 8b in the base plate 3, and the annular groove 3b in the base plate 3 into the area of the central opening 3c in the base plate 3. The bypass air will then be drawn into the inner conduit 5a and outlet 5b of the mouthpiece 5, together with the medicament-laden main air stream from the receptacle 4.

Figure 6A:
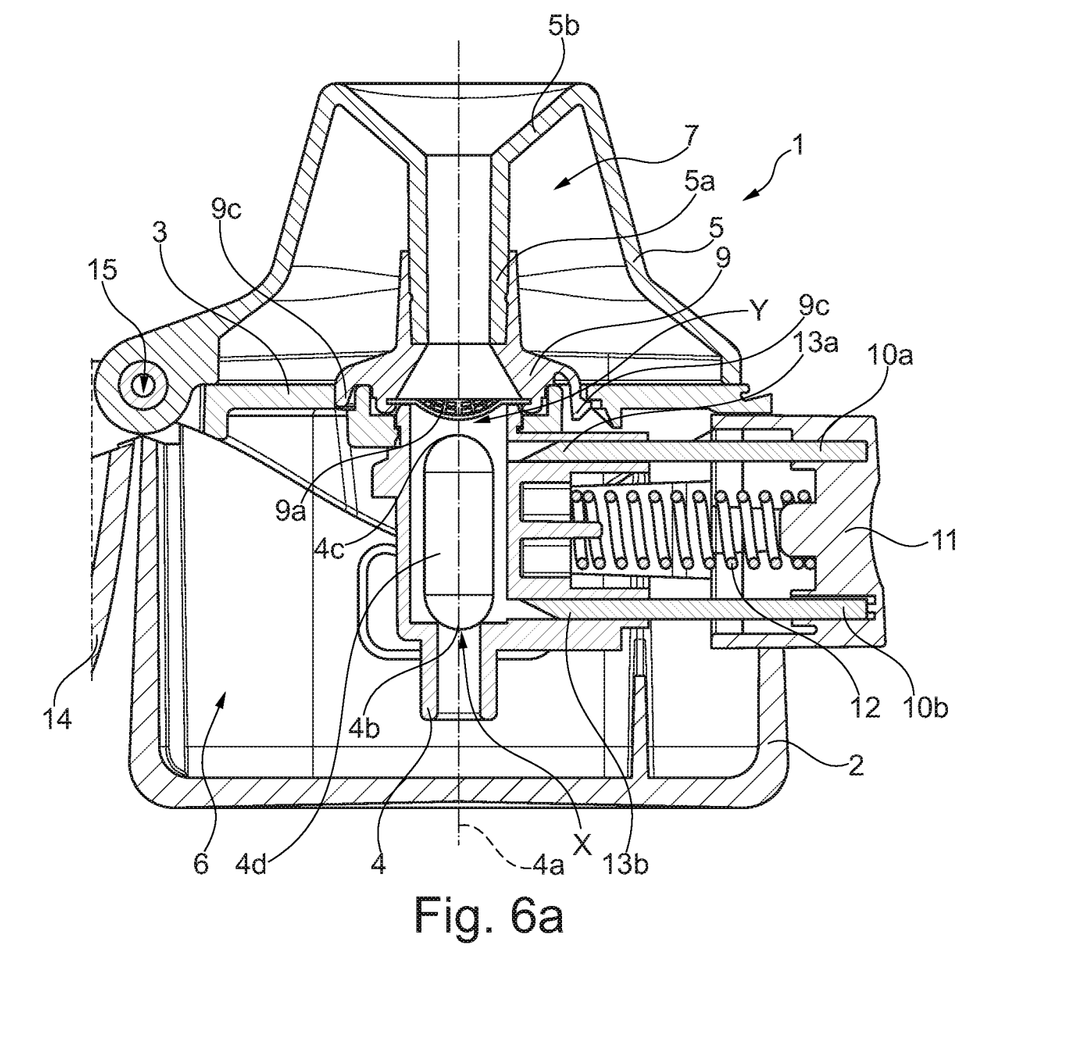
Figure 6B:
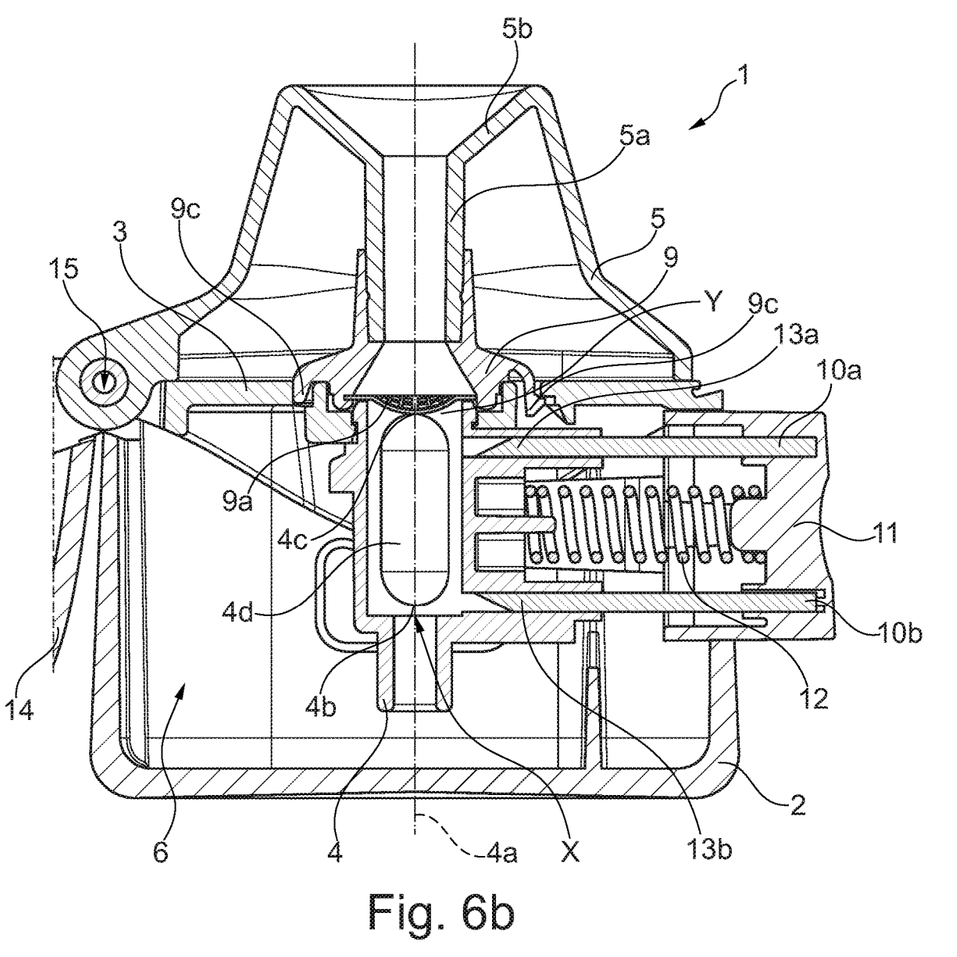

FIGS. 6a and 6b show simplified sectional views of the inhaler 1, to illustrate the influence of the reciprocating movement (shuttling) of the capsule 4d along the longitudinal axis 4a of the receptacle 4 on the flow resistance of the inhaler 1. The flow resistance can be calculated by dividing the square root of the pressure drop in the mouthpiece by the flow rate (volume per unit time) through the inhaler 1. The resistance along the main air flow path from the main space 6 through the receptacle 4 and the screen 9a on to the mouthpiece 5 has the largest single influence on the total flow resistance of the inhaler 1.

FIG. 6a illustrates the lower point of the shuttling motion, where the bottom end 4b of the capsule 4d is in the position marked X. In this position, the air inlet from the main space 6 to the receptacle 4 via the bottom of the reservoir 4 is partially or completely blocked by the capsule 4d, so the instantaneous flow resistance is extremely high.

In this position, the capsule 4d experiences an upward pressure force, in the direction from X to Y. This pressure differential is caused because the suction from the mouthpiece 5 creates a relatively low pressure at the top 4c of the capsule 4d, whereas the atmospheric pressure of the main space 6 creates a relatively high pressure on the bottom 4b of the capsule 4d.

This pressure force causes the capsule 4d to accelerate to the position shown in FIG. 6b, where the top 4c of the capsule 4d abuts against the screen 9a. In this position, the flow resistance of the inhaler 1 is not significantly influenced by the presence of the capsule 4d; i.e., the instantaneous resistance is the same as that measured without the capsule 4d present.

In this position, the capsule 4d experiences a downward pressure force, i.e., from Y to X. This pressure force is caused by the flow field that is set up around the hemispherical bottom 4b of the capsule 4d. The air jet entering the receptacle 4 at its bottom impinges on the bottom 4b of the capsule 4d and accelerates around this bottom 4b, creating an annular region of very low pressure.

This pressure force causes the capsule to accelerate back to the position shown in FIG. 6a, and the movement starts anew.

Therefore, the measured flow resistance of the inhaler 1 is a time-averaged resistance over a number of shuttling cycles. This time-averaged resistance will always be greater than the resistance measured without a capsule 4d present. The time-averaged resistance will be influenced by the rate of shuttling. A high shuttling rate will result in a relatively high resistance; a low shuttling rate will result in a relatively lower resistance. In the extreme where there is no shuttling (i.e., the capsule 4d remains fixed in the position shown in FIG. 6b), the measured resistance will be equal to the resistance measured without a capsule 4d.

The key design variable for influencing the rate of shuttling, and hence its contribution to flow resistance, is the length of the receptacle 4, and hence of the longitudinal path along which the capsule 4d may travel. Increasing the length of the receptacle 4 reduces the downward pressure force experienced by the capsule 4d in the position shown in FIG. 6b, which will reduce the rate of shuttling and hence the resistance. In addition, the increased length also increases the shuttling distance, which further reduces the rate of shuttling and hence the resistance.

What is claimed is:

1. A dry powder inhalation device, comprising: a housing, a base plate, a receptacle for a medicament and a mouthpiece, wherein the base plate is engageable with the housing to form a main space with a main air inlet, the mouthpiece comprises an inner conduit connected to its outlet, the mouthpiece is engageable with the base plate to fluidly connect the inner conduit to the receptacle, and the receptacle is fluidly connected to the main space, so that upon inhalation by a user, air can be drawn through the main air inlet into the main space and onward through the receptacle into the inner conduit, wherein the mouthpiece and the base plate form an auxiliary space with an auxiliary air inlet, wherein the auxiliary space is fluidly connected to the main space, wherein the base plate comprises at least one air exchange opening for connecting the auxiliary space to the main space, wherein flow resistance of each of the main air inlet and the auxiliary air inlet is lower than flow resistance of a path between the main space and the mouthpiece outlet and lower than flow resistance of a path between the auxiliary space and the mouthpiece outlet, the housing having an oval shape comprising two flat side faces and two curved side faces, the two flat side faces being larger than the two curved side faces.

2. The device according to claim 1, wherein the main air inlet, and/or the auxiliary air inlet, comprises a recess in the base plate.

3. The device according to claim 2, wherein the recess comprised in the main air inlet is formed in an area where the base plate is hinged to the housing.

4. The device according to claim 2, wherein the recess comprised in the auxiliary air inlet is formed in an area where the base plate is set in a further recess in the housing.

5. The device according to claim 4, wherein the further recess is placed in at least one of the flat side faces.

6. The device according to claim 1, wherein the inner conduit is connectable to the receptacle via a screen held in a screen holder.

7. The device according to claim 1, further comprising at least one piercing element that is movable into the receptacle by pushing a button against the force of a spring.

8. The device according to claim 1, wherein the housing, the base plate and the mouthpiece are hinged about a common axis of rotation.

9. The device according to claim 1, wherein a first airway is provided between the main space and atmosphere, so that upon inhalation by a user, air can be drawn through the first airway into the main space and onward through the receptacle into the inner conduit, wherein the auxiliary space is fluidly connected to atmosphere by a second airway and to the inner conduit by a bypass air path.

10. The device according to claim 9, wherein flow resistance of the bypass air path is lower than flow resistance of the combination of all leakage paths in the device.

11. The device according to claim 9, wherein the inner conduit is connectable to the receptacle via a screen held in a screen holder.

12. The device according to claim 9, wherein the bypass air path comprises at least one opening and/or recess (8a) in the screen holder.

13. The device according to claim 12, wherein the bypass air path further comprises at least one opening and/or recess in the base plate that cooperates with the opening and/or recess in the screen holder.

14. The device according to claim 12, wherein the screen holder has a circular circumference, and the bypass air path comprises at least four openings and/or recesses in a symmetric arrangement of angular positions along this circumference.

15. The device according to claim 12, wherein the recesses are located in a perimeter of the screen holder.

16. The device according to claim 15, wherein at least one recess in the perimeter of the screen holder cooperates with the base plate to enclose a channel with a cross sectional area above 0.2 mm$^2$ and below 0.8 mm$^2$.

17. The device according to claim 12, wherein at least one opening in the screen holder is a hole with a diameter above 0.5 mm and below 1 mm.

18. The device according to claim 11, wherein the screen holder is click-mountable to the mouthpiece.

19. The device according to claim 9, wherein the base plate comprises at least one air exchange opening for connecting the auxiliary space to the main space.

20. The device according to claim 9, further comprising at least one piercing element that is movable into the receptacle by pushing a button against the force of a spring.

21. The device according to claim 20, wherein the housing has a recess to accommodate the button.

22. The device according to claim 20, wherein at least one end stop is provided for the piercing element to keep it from completely traversing the receptacle.

23. The device according to claim 20, wherein a first piercing element with a first chamfered tip and a second piercing element with a second chamfered tip are provided, wherein the chamfers of the two tips have opposite orientations towards the longitudinal axis of the receptacle.

24. The device according to claim 9, wherein the housing, the base plate and the mouthpiece are hinged about a common axis of rotation.

25. The device according to claim 24, further comprising a lid for covering the mouthpiece when the device is not in use, wherein the lid is hinged about the same axis of rotation.

26. A dry powder inhalation device, comprising: a housing, a base plate, a screen holder situated on the base plate, a receptacle for a medicament and a mouthpiece, wherein the base plate is engageable with the housing to form a main space with a main air inlet, the mouthpiece comprises an inner conduit connected to its outlet, the mouthpiece is engageable with the base plate to fluidly connect the inner conduit to the receptacle, and the receptacle is fluidly connected to the main space, so that upon inhalation by a user, air can be drawn through the main air inlet into the main space and onward through the receptacle into the inner conduit, wherein the mouthpiece and the base plate form an auxiliary space with an auxiliary air inlet, wherein the auxiliary space is fluidly connected to the main space, wherein the base plate comprises at least one air exchange opening for connecting the auxiliary space to the main space, wherein flow resistance of each of the main air inlet and the auxiliary air inlet is lower than flow resistance of a path between the main space and the mouthpiece outlet and lower than flow resistance of a path between the auxiliary space and the mouthpiece outlet, wherein the auxiliary space is fluidly connected to the inner conduit by a bypass air path, the bypass air path being formed by cooperation between a portion of a hole formed in the base plate and a portion of a hole formed in the screen holder.

27. A dry powder inhalation device, comprising: a housing, a base plate, a receptacle for a medicament and a mouthpiece, wherein the base plate is engageable with the housing to form a main space with a main air inlet, the mouthpiece comprises an inner conduit connected to its outlet, the mouthpiece is engageable with the base plate to fluidly connect the inner conduit to the receptacle, and the receptacle is fluidly connected to the main space, so that upon inhalation by a user, air can be drawn through the main air inlet into the main space and onward through the receptacle into the inner conduit, wherein the mouthpiece and the base plate form an auxiliary space with an auxiliary air inlet, wherein the auxiliary space is fluidly connected to the main space, wherein the base plate comprises at least one air exchange opening for connecting the auxiliary space to the main space, wherein flow resistance of each of the main air inlet and the auxiliary air inlet is lower than flow resistance of a path between the main space and the mouthpiece outlet and lower than flow resistance of a path between the auxiliary space and the mouthpiece outlet, wherein the auxiliary space is fluidly connected to the inner conduit by a bypass air path having a bypass opening, and wherein the at least one air exchange opening is at least one of a different shape and a different size than the bypass opening.

* * * * *